US00RE34644E

United States Patent [19]

Flehmig

[11] E Patent Number: Re. 34,644

[45] Reissued Date of Patent: Jun. 21, 1994

[54] HEPATITIS-A VIRUSES ADAPTED TO HUMAN FIBROBLAST CELLS

[76] Inventor: Bertram Flehmig, Horemer 21, D-7400 Tübingen, Fed. Rep. of Germany

[21] Appl. No.: 550,635

[22] Filed: Jul. 10, 1990

Related U.S. Patent Documents

Reissue of:

[64] Patent No.: 4,506,016
Issued: Mar. 19, 1985
Appl. No.: 415,524
Filed: Sep. 7, 1982

[30] Foreign Application Priority Data

Sep. 9, 1981 [DE] Fed. Rep. of Germany ..... 3135599

[51] Int. Cl.[5] ..... A61K 39/29; C12N 7/08

[52] U.S. Cl. ..... 435/237; 424/89; 435/235.1

[58] Field of Search ..... 435/237, 235.1; 424/89

[56] References Cited

U.S. PATENT DOCUMENTS 4,164,566 8/1979 Provost et al. .

FOREIGN PATENT DOCUMENTS 2398504 7/1977 European Pat. Off. .
025745 9/1980 European Pat. Off. .
71119A1 9/1982 European Pat. Off. .
2398504 2/1979 France .

OTHER PUBLICATIONS

Feinstone, et al., Science vol. 182, pp. 1026–1028, (1973).

*Primary Examiner*—David Saunders
*Attorney, Agent, or Firm*—Jacobson, Price, Holman & Stern

[57] ABSTRACT

Hepatitis-A virus, suitable for use in human or animal vaccines, is prepared by adapting the virus first to human kidney cells and subsequently adapting the thus-altered virus to human fibroblast strains. In the process the growth rate of Hepatitis-A virus on the noted tissues is materially increased. This HAV is also a useful antigen in diagnostic test procedures.

20 Claims, No Drawings

HEPATITIS-A VIRUSES ADAPTED TO HUMAN FIBROBLAST CELLS

Matter enclosed in heavy brackets [ ] appears in the original patent but forms no part of this reissue specification; matter printed in italics indicates the additions made by reissue.

German patent application (DE-OS) No. P 30 33 406.6 (published Apr. 15, 1982) describes a method for making Hepatitis-A Virus (HAV). The growth of HAV can now be accelerated by seeding HAV on Rhesus monkey kidney cells (FrhR-4/R), harvesting resulting viruses which appear after several weeks and subsequently similarly seeding the resulting viruses again. This process is repeated until the obtained viruses have a satisfactory rate of growth.

Resulting HAV are unsuited for vaccines for human medicine because they come from animal cells.

SUMMARY OF THE INVENTION

There are a number of distinct aspects of this invention, all of which make possible vaccine (derived from Hepatitis-A virus) for human medicine, which is one aspect and a principal object. A further principal object is the use of the cell culture produced HAV as an antigen in diagnostic test procedures. Other aspects include:

(a) selecting tissue for sequential culturing of HAV, (b) adapting HAV to human kidney cells (HKC), (c) increasing the growth rate of HAV on HKC, (d) HAV/HKC, (e) adapting HAV/HKC to human fibroblast strains (HFS), (f) increasing the growth rate of HAV/HKC on HFS, (g) HAV/HFS and (h) HAV/HFS antigens and antibodies produced therefrom.

Beyond these noted aspects, operating equipment, parameters and procedures, tissue preparation and culturing, culture media, virus inoculation and culturing, detection and analysis methods and equipment, preparing antigens, producing antibodies, harvesting viruses and antibodies and formulating and administering vaccine are substantially conventional and well within the skill of the art.

The main purpose of this invention is to prepare HAV which can be used in human medicine. Such viruses are Hepatitis-A viruses, HAV/HFS, which are adapted to human fibroblast strains (HFS) via human embryo kidney cells (HKC). Their production is accomplished by culturing HAV on HKC, harvesting resulting viruses, culturing thus-harvested viruses on HKC and repeating this procedure to obtain HAV/HKC having an acceptable growth rate. The HAV/HKC is then cultured on HFS, harvesting resulting viruses and similarly repeating the culturing and harvesting to obtain HAV/HFS.

DETAILS

Attempts to propagate unmodified HAV isolate of human origin from clinical specimens in fibroblast cultures were unsuccessful. Over a period of fifteen weeks no HAV was detected (by RIA or immunofluorescence methods) in infested cells. HAV adapted to HKC over ten passages (HAV/HKC), however, was successfully propagated in human fibroblast; four weeks after inoculation with HAV/HKC the first supernatant of HFS (positive for HAV) was detected with RIA (radioimmunoassay). Further adaptation of HAV/HKC to human fibroblast strains was achieved by seeding the first positive (for HAV) supernatant on HFS and repeating the procedure as was done to adapt HAV to HKC.

HAV isolated from stool (unmodified HAV) is cultured in HKC. Conventional methods, such as those described in the previously-noted patent application No. P 30 33 406.6, are employed. The first viruses released (after about seven or eight weeks) are used, once again, to inoculate HKC (passage 2 in HKC). This process is repeated for about ten passages, with an increase in growth rate resulting from each successive passage. The viruses, which grow rapidly and in large quantities, are selected in each case.

HAV adapted to HKC (HAV/HKC) is thus obtained for the first time. The HAV/HKC is a modified HAV.

It is most surprising that:

1. viruses can be harvested at all after a comparatively long interval of time; as the usual rate of growth is considerably higher, the improbability of such a process is apparent rather soon; and 2. adoption to HKC with a high rate of growth is achieved through repeated passages.

These procedures are repeated in connection with infection of human fibroblast cells (HFS) with HAV/HKC. Here again, HAV/HKC grows at a very low rate in its first passage in HFS; eventual success is thus entirely unexpected.

By means of repeated passages of HAV/HKC on HFS, HAV is finally adapted to HFS; in other words, HAV/HFS is eventually harvested both from the cell and from the nutrient medium.

The HAV/HFS is equally suitable for use in tests with HAV antibodies and, above all, for making vaccine for human medicine.

The invention is explained in greater detail in the following examples:

EXAMPLE I

Hepatitis-A Virus Isolates

Stool suspensions containing HAV strains, GBG, GBM and GJA, are used. The origin of these isolates is described by Flehmig et al. (1977). Stool suspensions are prepared as 2.5 percent suspensions with Hanks' balanced salt solution, as described by Flehmig et al. (1977).

The 2.5 percent suspensions are buffered at pH 7.2 with phosphate buffered saline (PBS) and partially cleared by centrifugation at 3000 G and again at 6000 G for 30 minutes each. The final supernatant is designated "fecal extract".

Cells and HAV/GBM were deposited at Paul-Ehrlich Institute, Frankfurt/Main, on Jul. 15, 1981.

EXAMPLE II

Cell Cultures

Kidneys and lungs from human embryos (10 to 25 weeks old) are processed according to established procedures for producing human kidney cells (HKC) and human fibroblast strains (HFS). Cell cultures are established by conventional procedures using TC 199 Hanks' plus 10 percent fetal calf serum for HKC and MEM Hanks' plus 7 percent fetal calf serum for HFS as growth media. It is possible to subpass the first monolayer stratum of kidney cells at least 5 times, e.g. from 5 to 10 times, and of fibroblast strains over 50 times, e.g. from 50 to 75 times. Parts of the first passage of HKC and of HFS are optionally frozen according to well-known methods at −70° C. or in liquid nitrogen, thawed when needed and subsequently used.

EXAMPLE III

Cultivating HAV in HKC and HFS

Densely-grown monolayer strata of HKC or HFS are incubated with HAV-containing suspensions, and the viruses are absorbed by the cells. After that, suitable nutrient medium is placed on cells, which are incubated at from 34° to 37° C. After corresponding incubation times, the quantity of HAV, which is extracted from the cells into the nutrient medium, is determined by means of suitable conventional analysis methods. The extracted HAV is useful for test methods to establish the presence of antibodies in human or animal serums or, according to certain purification and inactivation methods, for vaccine for man and animals.

EXAMPLE IV

Adaptation of HAV to HKC

Five weeks after inoculating HKC (cf. Example II), with HAV (first passage through), the first supernatant (positive for HAV) is detected by RIA. To select the more rapidly growing viruses, the first HAV-positive supernatant detected for each passage is used as inoculum for the next passage on HKC. The time between inoculation of HAV and detection of the first HAV-positive supernatant is gradually reduced with each successive passage.

The first HAV-positive supernatant obtained (first passage) for HKC inoculated with HAV is detected, e.g., by RIA 34 days after infection of the cells. In the tenth passage the first HAV-positive supernatant is detected by RIA about 6 days after infection.

Cell-bound viruses are harvested by freezing and thawing the cells three times with 10 percent (by volume) of the supernatant to produce a concentrate. The amount of HAV in the resulting thawed product is thus greater than that previously in cell-bound form.

In this experiment the first cell lysate positive for HAV (ninth passage through HKC) was detected by RIA five days after infection; the first supernatant positive for HAV, eight days after infection. In another experiment the first supernatant positive for HAV (ninth passage through HKC) was detected six days after infection; the first supernatant positive for HAV (18th passage through HKC) was detected by RIA four days after inoculation.

HAV adapted to HKC during ten passages is designated HAV/HKC.

EXAMPLE V

Adaptation of HAV to HFS

Following the procedures of Example IV, HFS is inoculated with HAV/HKC, the first supernatant positive to HAV/HKC is used to inoculate HFS, and the steps are repeated until Hepatitis-A viruses adapted to human fibroblast cells (HAV/HFS) are obtained.

To produce HAV/HFS for vaccine purposes an effective amount of immunity-inducing HAV-antigen is used.

EXAMPLE VI

Harvesting Cell-Bound Virus and Detecting Virus in the Supernatant

Remove maintenance medium from cells and cultured virus in a 75 cc flask. Add 3 ml of Hanks' balanced salt solution to the flask. Freeze and thaw (three times) the cells and Hanks' solution. Clear the resulting product by centrifugation for 30 minutes at 3,000×G. Use the obtained supernatant for detecting HAV/AG by RIA. The virus antigen detected this way is regarded as cell-bound virus.

To measure the amount of virus in the supernatant, 100 microliters of maintenance medium is subject to RIA without prior treatment.

EXAMPLE VII

Radioimmunoassay (RIA) for HAV Detection

Using the RIA procedure of Purcell et al. (1976); which has been described in detail by Flehmig (1978) and by Flehmig et al. (1978), a solid phase (PVC U-plates, Dynatech, Nuertingen/FRG) is coated with an ANTI-HAV. After three wash steps, the suspension to be tested for HAV is poured into the wells. After an overnight incubation period at room temperature, the cups are washed and a purified human IgG preparation with a high concentration of ANTI-HAV labeled with radioactive I-125 (150,000 counts per minute (cpm)) is added into two wells together with an ANTI-HAV positive serum and into two wells together with an ANTI-HAV negative serum. The microliter plates are subsequently incubated at 37° C. for 6 hours.

Antigen samples are considered to be positive if values greater than 2.1 are obtained by dividing the CPM of two test samples from ANTI-HAV negative serum by the CPM of two test samples from ANTI-HAV positive serum; the P/N ratio by the competitive binding technique with ANTI-HAV positive and ANTI-HAV negative serum insures the specificity of each test run.

EXAMPLE VIII

Radioimmunoassay for Detection of ANTI-HAV

For measuring ANTI-HAV IgG, the solid-phase is coated with ANTI-HAV in the manner referred to in Example VII. A defined amount of HAV is bound to the antibody layer in the previously-described manner. 0.05 mi of serum to be tested and 0.05 ml of I-125-labeled ANTI-HAV IgG are placed into each cup simultaneously.

Reduction in residual radioactivity, as compared with a pre-illness serum, is determined. A reduction of 50 percent or more is considered to be positive.

EXAMPLE IX

RIA for Detection of IgM Antibody to HAV

The solid phase (PVC-U plates) are coated with 100 microliters of rabbit antiserum to human IgM [diluted to a concentration of 5×0.01 in phosphate-buffered saline (PBS), pH 7.2, containing 0.1 percent sodium] per well. After incubation for 24 hours at room temperature (about 24° C.), 10 microliters of calf serum are added to each well to saturate the solid phase. The coated plates are then used directly or stored for several weeks at 4° C. Sera to be tested for IgM antibody to HAV are serially diluted: 0.01, 0.001, 0.0001, 0.00001 and 0.000001, in PBS, pH 7.2. After the wells are rinsed three times with PBS (pH 7.2), each well is charged with 100 microliters of each dilution of serum. Nonspecific binding is determined with eight wells by adding 100 microliters of 1 percent pooled human serum devoid of antibody to HAV diluted in 3 percent calf serum in PBS.

After incubation for from 6 to 8 hours at 37° C., the wells are washed three times with PBS, pH 7.2. Then each well is charged with 100 microliters of a suspension of HAV, and the plates are incubated overnight at room temperature. After three more washes, 100 microliters of a solution of (I-125) IgG antibody to HAV (giving 150,000 CPM) is added to each well, and the plates are incubated at 37° C. for 6 hours. Finally, the wells are washed three times with PBS (pH 7.2), and the radioactivity of each well is measured with a gamma counter [Kontron, Munich, German Federal Republic (FRG)]. Sample counts exceeding five times the counts obtained with the nonspecific-binding wells are considered to be significant (positive for antibody to HAV). After optimization, the preceding procedure was performed.

The same principles prevail when the employed tracer is an ANTI-HAV-IgG or Anti-HAV-F(ab)2 labelled with peroxidase or phosphatase.

Hepatitis-A viruses (HAV) adapted to human) fibroblast strains (designated HAV/HFS) are deposited with the Paul Ehrlich Institute, Frankfurt/Main.

The invention and its advantages are readily understood from the preceding description. Various changes may be made in the procedures, equipment, operating parameters and testing procedures without departing from the spirit and scope of the invention or sacrificing its material advantages. The processes and products hereinbefore described are merely illustrative of preferred embodiments of the invention.

What is claimed is:

1. A process which comprises culturing unmodified HAV on human kidney cells (HKC) and harvesting [the thus-] produced *cell-free* viruses.

2. A process which comprises culturing on HKC isolated *cell-free* viruses produced by the process of claim 1 and isolating thus-produced *cell-free* viruses.

3. A process for increasing the growth rate of HAV cultured on HKC which comprises (a) the process of claim 2, (b) culturing the resulting isolated *cell-free* viruses on HKC and isolating thus-produced *cell-free* viruses and (c) repeating step (b) a number of times, each with isolated *cell-free* viruses from the immediately preceding culturing on HKC.

4. A process of claim 3 which comprises from about five to ten successive culturing steps.

5. A process according to claim 2 or claim 3 which comprises isolating from the final culturing step those viruses which grow most rapidly and/or are produced in largest quantities.

6. A process according to claim 2 or claim 3 which comprises (a) selecting from each culturing step those viruses which grow most rapidly and/or are produced in largest quantities and (b) culturing only thus-selected viruses in any immediately succeeding culturing step.

7. A process of claim 1 wherein the HAV is Hepatitis-A virus isolate of human origin.

8. A process of claim 7 wherein the HAV consists essentially of that isolated from stool.

9. A process of claim 1 which consists essentially of culturing HAV on HKC.

10. Modified HAV adapted to HKC (HAV/HKC) and having a rate of growth and/or a rate of proliferation significantly greater than that of unmodified HAV cultured on HKC.

11. A process which comprises culturing the modified virus of claim 10 on human fibroblast strains (HFS).

12. A process which comprises culturing on HFS isolated viruses produced by the process of claim 11 and isolating thus-produced viruses.

13. A process for increasing the growth rate of HAV/HKC cultured on HFS which comprises (a) the process of claim 12, (b) culturing the resulting isolated viruses on HFS and isolating thus-produced viruses and (c) repeating step (b) a number of times, each with isolated viruses from the immediately preceding culturing on HFS.

14. A process of claim 13 which comprises from about 50 to 75 successive culturing steps.

15. A process according to claim 13 or claim 14 which comprises (a) selecting from each culturing step those viruses which grow most rapidly and/or proliferate in greatest quantities and (b) culturing only thus-selected viruses in any immediately succeeding culturing step.

16. Modified HAV according to claim 10 and further adapted to HFS (HAV/HFS) and having a rate of growth and/or a rate of proliferation significantly greater than that of modified HAV according to claim [8] *10* and cultured on HFS.

17. A process which comprises:

(a) culturing unmodified HAV on human kidney cells (HKC) and harvesting thus-produced viruses, (b) culturing isolated viruses from step (a) on EIKC and isolating thus-produced viruses, (c) culturing isolated viruses from step (b) on HKC and isolating thus-produced viruses, (d) repeating step (c) a number of times, each with isolated viruses from the immediately preceding culturing on HKC to obtain HAV adapted to HKC (HAV/HKC) and having a rate of growth and/or a rate of proliferation significantly greater than that of HAV cultured on HKC, the isolated viruses cultured in and isolated from the products of steps (b) through (d) being those which grow most rapidly and/or are produced in largest quantities;

(e) culturing HAV/HKC isolated from step (d) on human fibroblast strains (HFS) and isolating thus-produced viruses, (f) culturing isolated viruses from step (e) on HFS and isolating thus-produced viruses, (g) culturing isolated viruses from step (f) on HFS and isolating thus-produced viruses, (h) repeating step (g) a number of times, each with isolated viruses from the immediately preceding culturing on HFS to obtain HAV adapted to HFS (HAV/HFS) and having a rate of growth and/or a rate of proliferation significantly greater than that of HAV/HKC cultured on HFS, the isolated viruses cultured in and isolated from the products of steps (e) through (h) being those which grow most rapidly and/or are produced in largest quantities.

*18. A process which comprises culturing unmodified HAV on human kidney cells (HKC) in a culture medium until supernatant in the culture medium is positive for HAV, inocculating fresh HKC with the supernatant, culturing again until supernatant is positive for HAV, and harvesting thus-produced viruses from the latter supernatant.*

*19. A process of claim 1 which comprises culturing unmodified HAV on human kidney cells (HKC) and harvesting, directly from culture supernatant, produced cell-free viruses which are free from cell particles without further separation.*

*20. A process of claim 1 which comprises culturing unmodified HAV on human kidney cells (HKC) until cell-free viruses pass through intact cell walls into culture supernatant, and harvesting produced cell-free viruses from the supernatant.*

* * * * *